(12) United States Patent
Boulanger et al.

(10) Patent No.: US 6,821,269 B1
(45) Date of Patent: *Nov. 23, 2004

(54) SANITARY ABSORBENT ARTICLE HAVING FLAPS

(76) Inventors: Roger Boulanger, 1848 De Bourgogne, Ste-Julie, Quebec (CA), J3E 1C5; Henri Brisebois, 2129 Florent, Lachenaie, Quebec (CA), J9W 5W6

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 213 days.

(21) Appl. No.: 09/290,305

(22) Filed: Apr. 12, 1999

Related U.S. Application Data (63) Continuation-in-part of application No. 09/071,504, filed on May 1, 1998, now abandoned.

(51) Int. Cl.$^7$ ................................................ A61F 13/15
(52) U.S. Cl. .................... 604/385.04; 604/387; 604/389
(58) Field of Search .................... 604/389, 358, 604/387, 385.01, 385.04, 386, 385.05; 24/442, 452, 306

(56) References Cited

U.S. PATENT DOCUMENTS

| | | | |
|---|---|---|---|
| 4,285,343 A | | 8/1981 | McNair |
| 4,589,876 A | * | 5/1986 | Van Tilburg ................ 604/385 |
| 4,608,047 A | * | 8/1986 | Mattingly .................... 604/387 |
| 4,900,320 A | * | 2/1990 | McCoy ........................ 604/387 |
| 5,217,448 A | * | 6/1993 | Glaug et al. ................. 604/397 |
| D348,514 S | | 7/1994 | Pearlstein et al. |
| 5,611,790 A | | 3/1997 | Osborn, III et al. |
| 5,921,975 A | * | 7/1999 | Suzuki et al. ............. 604/385.2 |

FOREIGN PATENT DOCUMENTS

| | | |
|---|---|---|
| EP | 0 446 818 A2 | 9/1991 |
| EP | 0 496 709 A1 | 7/1992 |
| EP | 0 511 905 A1 | 11/1992 |
| EP | 0 571 961 B1 | 12/1993 |
| GB | 2 284 993 A | 6/1995 |
| JP | 728981 | 4/1988 |
| JP | 903761 | 7/1994 |
| JP | 925624 | 5/1995 |
| WO | WO 92/18080 A1 | 10/1992 |
| WO | WO 94/14398 A2 | 7/1994 |
| WO | WO 96/00546 A1 | 1/1996 |

* cited by examiner

Primary Examiner—Dennis Ruhl
Assistant Examiner—Michele Kidwell (57) ABSTRACT

A sanitary absorbent article having flaps which substantially continually diverge from their proximal side over large portion of their length, preferably until their distal side. The substantially continually divergent portions being preferably substantially straight. The garment-facing surface of the flaps including an adhesive fastener which has a length not less than 85% of the length of the proximal side, and preferably not less than 100% of the length of the proximal side. The fastener preferably having reduced adhesive strength in the zones nearer the transverse sides of the flap.

8 Claims, 4 Drawing Sheets

SANITARY ABSORBENT ARTICLE HAVING FLAPS

This application is a continuation-in-part of application Ser. No. 09/071,504, field May 1, 1998, now abandoned.

FIELD OF THE INVENTION

The present invention relates to sanitary absorbent articles such as feminine sanitary napkins and incontinence pads, and, more particularly, to sanitary absorbent articles having side-projecting flaps.

BACKGROUND OF THE INVENTION

Sanitary absorbent articles generally are large-scale commercially-manufactured articles used to absorb and retain a variety of bodily exudates. Such articles are convenient in that they are often economical yet disposable; they include sanitary napkins, infant diapers, adult incontinence pads and the like.

The technology surrounding sanitary absorbent articles, and particularly feminine sanitary napkins, has undergone several advances over the past two decades. One of such advances was the addition of a flap projecting laterally from each longitudinal side of the article when the article is in a flattened state. Such flaps may comprise integral extensions of a material from which the article is formed or, alternatively, may simply comprise additional material added to the article after its formation.

When such articles are in use, the flaps are folded over the edges of the wearer's undergarment. They thus may more firmly secure the article to the undergarment, stabilize the article within the undergarment, provide an increased absorptive area for bodily exudates, and help prevent the undergarment from becoming soiled in part by protecting the side edges of the wearer's undergarment. The flap concept has generally met with success in the marketplace, and articles with flaps of various configurations and conformations are available to the consumer.

Conventional wisdom on the part of both designers and consumers has to date dictated that flaps on absorbent articles should be maximized at their line of juncture with the main body of the article in order to provide a greater area of protection against exudate leakage over the side of the article. Hence, a very common flap configuration is an isosceles (i.e. bilaterally symmetrical) trapezoidal-shaped flap having its base adjoined with the longitudinal side of the main body of the article and projecting (and tapering) away therefrom to the top of the trapezoid. The size of the flap may vary from article to article. Other prior art flap shapes may be loosely described as rectangular, square or mushroom-shaped.

The difficulty with absorbent articles of the trapezoidal and other conventional flap configurations is that the absorbent articles are designed and manufactured in a flat state, while in use the article should generally adopt a two- and often three-dimensional curvature in order to correctly interface with the body of the wearer. By two-dimensional curvature it is meant that the article will curve along one axis of the three-dimensional coordinate system formed by the longitudinal centre-line of the article, the transverse centre-line of the article, and the line perpendicular to both. By three-dimensional curvature it is meant that the article will curve along more than one axis of a three-dimensional co-ordinate system (such a system having three orthogonal axes).

As an example, where the absorbent article is a feminine sanitary napkin, and is in use, a cross-section of the article in both the sagital plane of the wearer's body (i.e. the longitudinal axis of the article) and the frontal or coronal plane of the wearer's body (i.e. the transverse axis of the article) would most likely be curved. The flaps, however, are generally designed to be folded about a linear folding axis commonly located along the line of juncture of the flap with the longitudinal side of the main body of the article. The difficulty with such a linear folding axis is that the edges of the wearer's undergarment, about which the flaps are folded, is curved. Moreover, the undergarment edges usually contain an elastic material for snugly securing the undergarment about the legs of the wearer. Depending on the force exerted by the elastic material, a curved shape may be imparted to the flaps and the central portion of the main body of the article causing them lift off the undergarment and wrinkle, or a flattened shape may be imparted to the edges of the undergarment causing them to not fit snugly against the legs of the wearer. In both cases, the comfort and efficiency of the article and its flaps are sacrificed. Moreover, the larger the flap, the more acute the problem. Thus while large flaps alleviate some difficulties on one hand (i.e. side leakage protection), they create problems on the other (i.e. instability and stress).

To date, most have thought that the benefits afforded by large flaps have outweighed their detriments, so they have been preferred. This has led to substantial efforts to attempt to overcome the difficulties associated therewith. As a result, many different solutions have been attempted in the past to resolve the problems of instability and stress present in absorbent articles of conventional flap design. None to date, however, has been completely satisfactory in that they have always yielded structures that are complex, expensive and/or complicated to manufacture. Moreover, they are often not comfortable for the wearer, or at least could be more comfortable.

An absorbent article having an improved flap configuration that would avoid, alleviate or relieve the stress created in conventional flap configurations as described above, yet while being relatively simple and inexpensive to manufacture is therefore desirable.

OBJECT AND STATEMENT OF THE INVENTION

It is thus an object of an aspect of the present invention to provide a sanitary absorbent article having an improved flap configuration.

It is a further object of an aspect of the present invention to provide a sanitary absorbent article having a flap configuration having relatively large flaps while having a reduced stress as compared with some of the prior art designs and all-the-while being relatively simple and/or inexpensive to manufacture.

It has been discovered by the present inventors, that, contrary to conventional wisdom, a flap having a configuration generally inverted from those of the prior art is indeed desirable. By inverted it is meant that the flap will generally constantly increase in width (i.e. being substantially constantly divergent) progressing from its proximal side to its distal side (i.e. it is inversely tapered). An example would be a generally isosceles trapezoidal-shaped being larger at its distal side that at its proximal side, i.e. the base of trapezoid being at the distal side of the flap. Such flaps provide the appearance of being relatively "large", yet have reduced stress and increased stability over the prior art flap designs; surprisingly without significantly affecting side leakage protection.

Thus, as embodied and broadly described herein, the present invention provides a sanitary absorbent article comprising:

(A) a main body, said main body having a first longitudinal side, a second longitudinal side generally opposing the first longitudinal side, two generally-opposing transverse sides, and a longitudinal centerline; and (B) a first flap united with said main body, said first flap projecting laterally from the first longitudinal side of said main body when the article is in a flattened state and being capable of being folded over a crotch portion of a wearer's undergarment, said first flap having:
  (i) a distal side;
  (ii) a proximal side generally opposing the distal side of said first flap, the proximal side being adjacent the first longitudinal side of said main body;
  (iii) a first transverse side;
  (iv) a second transverse side generally opposing the first transverse side of said first flap; and
  (v) a garment-facing surface including a fastener for securing said first flap to the garment;
    the first transverse side of said first flap and the second transverse side of said first flap being substantially continually divergent from the proximal side of said first flap until an imaginary line parallel to the longitudinal centerline of said main body at approximately a midpoint of said first flap.

Preferably, the sanitary absorbent article further comprises:

(C) a second flap united with said main body, said second flap projecting laterally from the second longitudinal side of said main body when the article is in a flattened state and being capable of being folded about the crotch portion of the undergarment, said second flap having:
  (i) a distal side;
  (ii) a proximal side generally opposing the distal side of said second flap, the proximal side being adjacent the second longitudinal side of said main body;
  (iii) a first transverse side;
  (iv) a second transverse side generally opposing the first transverse side of said second flap; and
  (v) a garment-facing surface including a fastener for securing said second flap to the undergarment;
    the first transverse side of said second flap and the second transverse side of said second flap being substantially continually divergent from the proximal side of said second flap until an imaginary line parallel to the longitudinal centerline of said main body at approximately a midpoint of said second flap.

Advantageously, (A) the first transverse side of said first flap and the second transverse side of said first flap are substantially straight from the proximal side of said first flap until the imaginary line thereof; and (B) the first transverse side of said second flap and the second transverse side of said second flap are substantially straight from the proximal side of said second flap until the imaginary line thereof Of further advantage, (A) the first transverse side of said first flap and the second transverse side of said first flap are substantially continually divergent from the proximal side of said first flap until the distal side of said first flap; and (B) the first transverse side of said second flap and the second transverse side of said second flap are substantially continually divergent from the proximal side of said second flap until the distal side of said second flap.

Of still further advantage, (A) the first transverse side of said first flap and the second transverse side of said first flap are substantially straight from the proximal side of said first flap until the distal side of the first flap; and (B) the first transverse side of said second flap and the second transverse side of said second flap are substantially straight from the proximal side of said second flap until the distal side of said second flap.

It is preferred that the main body of the article be generally hourglass in shape with rounded ends. When the article is of such a conformation, the first and second transverse sides are the shorter opposing sides and will generally be arcuate. The first and second longitudinal sides are the longer opposing sides and will generally be biconcavely curved. It should be understood however that the shape of such sides is not essential to the invention, and thus the transverse or the longitudinal sides could be either arcuate or straight. Nor is it essential that the main body be generally hourglass-shaped, as articles having main bodies in the shape of a square, rectangle, parallelogram or any other polygon, or even that of an oval or dog-bone, are all within the scope of the present invention. Where such is the case (i.e. where the main body is not rectangular), the longitudinal sides of the layer will be considered to be those opposing sides of a greater relative length as compared with the other opposing sides of the main body. Where it is impossible to make such a determination, any opposing pair of sides may be considered to be the longitudinal sides, or at the limit, opposing portions of any two sides may be considered to be the longitudinal sides. In either case, the transverse sides are the pair of opposing sides (or portions of sides) that are intersected by the longitudinal centre-line of the article, as that line is defined below.

For most articles, the longitudinal centre-line thereof is an imaginary line that extends along the longitudinal axis of the article and bisects the article into two identical or somewhat identical, yet not necessarily mirror image, halves. Similarly, the transverse centre-line is an imaginary line which is perpendicular to the longitudinal center-line and which ordinarily lies along the transverse axis of the article and bisects the article into two identical or somewhat identical, yet not necessarily mirror image, halves.

It is preferred that the flaps be of a generally trapezoidal shape, and still more preferred that the flaps be of the shape of an isosceles (i.e. bilaterally symmetrical) trapezoid. For present purposes, when the flap is of such a shape, it should be considered that the "top" of the trapezoid is the shorter of the two generally parallel sides, and that the "base" of the trapezoid is the longer of the two generally parallel sides. It should be understood that the term "generally parallel" is meant to encompass sides of a number of different conformations, including those which are slightly curved or angled and those which are formed from two or more straight edges joined at relatively wide angles.

It should expressly be understood, however, that such trapezoidal shape is not essential to the invention. Flaps in the shape of a variety of polygons are all within the scope of the present invention, and will yield similar benefits.

Flaps of the present invention may comprise an integral extension of the materials (or some of the materials) of which the main body of the article is formed. As an example, the flaps may comprise extensions of the cover layer material and the barrier layer material which are joined together, typically about the periphery of the flap. They may also comprise flaps constructed from panels which themselves comprise integral extensions of the materials of which the main body of the article is formed, having been re-affixed to the underside of the main body (i.e. on the garment facing-surface); all as described in commonly assigned co-pending International Patent Application PCT/CA97/00990, filed Dec. 22, 1997, herein incorporated by reference in its entirety. Alternatively, the flaps may comprise additional material added to the main body of the article after the main body's formation, typically secured to the garment-facing surface of the main body.

In any case, when the article is in a flattened shape (e.g when it is laid on a flat surface), the flaps project laterally from the longitudinal sides of the main body of the article outward (i.e. away from the longitudinal centreline of the article). The flaps are flexible and are capable of being folded about the edge of the crotch portion of a wearer's undergarment. A distal side of the flap is therefore the side of the flap which is generally opposing (and often parallel to) the longitudinal centreline of the main body and is the side of the flap that is furthest from the point of attachment of the flap to the main body, The distal side of the flap forms the base of the trapezoid (when the flap is trapezoidal shaped.). It is preferably straight or slightly arcuate, i.e. is substantially straight. It should be understood, however, that the distal side of the flap need not comprise a single line or curve. The distal side may thus comprise a series of two or more line segments and/or arcs joined together a relatively wide angles (i.e. greater than 120°).

Opposite the distal side (and thus in most circumstances intermediate the distal side and the longitudinal centerline) is the proximal side of the flap. Where the flap comprises an integral extension of the material from which the main body of the article is formed, and is not formed from a panel as described above, the proximal side of the flap will be adjoined with the longitudinal side of the main body. Alternatively, where the flap comprises additional material added to the main body after its formation and secured to the garment-facing surface thereof, or where the flap is formed from a panel as described above, the proximal side of the flap is the portion thereof which is adjacent to the longitudinal side of the main body. It will generally thus be that in such situations, the proximal side of the flap is not actually an edge of the flap. Where the proximal side cannot otherwise be defined, it should be considered to be the folding axis of the flap about the undergarment of a wearer of the article. In any case, the top of the trapezoid forms the proximal side of the flap (when the flap is trapezoidal shaped).

It should be understood that flaps constructed in accordance with the teachings of the present invention can have a proximal length of varying dimensions. A length of 6.2 cm is preferred, however, flaps having lengths of less than and greater than 6.2 cm, e.g. 3, 4, 5, 6, 7, 8, 9, 10, 11, 12, 13, 14, and 15 cm, are all within its scope.

The remaining two sides of the trapezoid form the first transverse side and second transverse side of the flap. They are substantially continually divergent from the proximal side of the flap until at least a line parallel to the longitudinal centreline at approximately the midpoint of the flap. The midpoint of the flap is the point equidistant from a first imaginary line connecting the point of intersection of the first transverse side of the flap with the distal side of the flap with the point of intersection of the second transverse side of the flap with the distal side of the flap, and a second imaginary line connecting the point of intersection of the first transverse side of the flap with the longitudinal side of the main body and the point of intersection of the second transverse side of the flap with the longitudinal side of the main body; and also equidistant from the first transverse side of the flap and the second transverse side of the flap.

Preferably, the first transverse side and the second transverse side are substantially continually divergent from the proximal side of the flap until at least the line along which the "longitudinal length" of the fastener of the flap (as defined hereinbelow) is measured.

Still more preferably, they are substantially divergent from the proximal side until the distal side. The expression "substantially continually divergent" in the context of the present invention should be understood as indicating a situation where the length of imaginary lines from the first transverse side of a flap to the second transverse side of the flap, parallel to the longitudinal centerline of the article, continually increase in a direction away from the proximal side towards the distal side.

Additionally, the substantially constantly divergent portions of the transverse sides are preferably substantially straight. Thus, the flaps would taper from their distal side to the proximal side, such that the distance between the two transverse sides (as measured along a line parallel to the longitudinal centerline of the article) steadily continually decreases from the distal side to the proximal side.

The article, including both the main body and the flaps, will have two opposing major surfaces. These surfaces may be identified by their position when the article is in use. That surface which faces, and is in contact with, the body of the wearer when the article is in use is termed the body-facing surface. The opposing surface is termed the garment-facing surface as in use it will typically face the garments of the wearer (or the external environment if the article is not covered by a garment).

Both the garment-facing surface of the main body and that of the flaps will typically include fasteners that are used to secure the article to wearer's garments. Advantageously, each of the fasteners located on the garment-facing surfaces of each flap has a longitudinal length not less than 85% of the length of the proximal side of the flap on which the fastener is located. In this context, the term "longitudinal length" should be understood as the maximum length of the fastener measured along a line parallel to the longitudinal centerline of the article. (For such purposes, gaps in the continuity of the fastener are ignored). The longitudinal length of the fastener may be colloquially termed its width.

It should be understood, however, that it is not necessary for the length of the fastener to exceed the length of the proximal along every line parallel to the longitudinal centerline of the article, only the "longitudinal length" along a single such line (at the maximum) will suffice.

Still more advantageously, the fastener has a longitudinal length greater than 85% of the proximal side of the flap on which the fastener is located. In this respect, longitudinal lengths of 85%, 90%, and 95% of the proximal side are respectively more preferred. Still even more advantageously the fastener has a longitudinal length not less than the length on the proximal side of the flap on which the fastener is located. In this respect, longitudinal lengths of 100%, 105%, 110% and 115% are respectively still more preferred.

It has been observed that when fasteners of these longitudinal lengths are employed, the central portion of the article has improved stabilization over prior art articles. By improved stabilization it is meant that the article will shift less with respect to the body when the article is in use by a wearer. It is believed that greater fastener longitudinal lengths contribute the stability of the central region of the article.

Preferably, when the article is in a flattened state,
(a) the transverse sides of said first flap each intersect with the first longitudinal side of said main body to form an angle of less than 90° and preferably not less than about 60°; and
(b) the transverse sides of said second flap each intersect with the second longitudinal side of said main body to form an angle of less than 90° and preferably not less than about 60°.

More preferably, each of these angles is approximately 75°.

It will be understood that the transverse sides of the flaps need not be substantially straight, but may rather be concavely arcuate. Where such is the case, the angle formed as described above should be understood as being the angle formed between the line tangent to the transverse side in question through the point of intersection of that transverse side with the appropriate longitudinal side, and the appropriate longitudinal side.

It has been surprisingly discovered that when the flaps are as described above, most of the benefits of large flaps are provided, however, some of the drawbacks have been alleviated. In this respect, a reduced amount of stress is present, the article is well stabilized within the undergarment of the wearer, and side-leakage protection has not been significantly sacrificed. Without wishing to be bound to any particular theory, it is believed that the stress which would have been created by flaps of the prior art is alleviated as the length of the flap along its folding-axis about the edge of the undergarment of the wearer is reduced relative to the distal edge. Moreover, the increased width of the flap in the distal area allows for the greater adhesive area to be present, and the shape of the flap allows for the total or near total amount of this adhesive to be effective, both of which better fasten the flap to undergarment, and thus secure the article within the undergarment.

Preferably, the fastener of said first flap and the fastener of said second flap each further comprise:
(1) a central zone having an adhesive strength; and
(2) a terminal zone having an adhesive strength, the adhesive strength of the terminal zone being less than the adhesive strength of the central zone.

In this respect, a fastener may loosely be divided into three zones, a first terminal zone closer to the first transverse side of the flap, a second transverse zone closer to the second transverse side of the flap, and a central zone intermediate the two terminal zones. As used herein, the term "zone" should be understood as including discontinuities (e.g. gaps) in the fastener which the length of such gaps is small relative to the longitudinal length of the fastener.

Moreover, in the preferred embodiment, the terminal zone of each of the fasteners does include a plurality of discontinuities (e.g. gaps) for reducing the adhesive strength of the terminal zone relative to the central zone. Other methods, however, will also suffice. For example, it would be possible to have the physical chemical properties of the adhesive in the terminal zone differ from that in the central zone (e.g. by having different chemical formulations). It would also be possible to coat the adhesive in the terminal zone with a substance, such as talc, which would partially bind to the adhesive reducing its overall adhesive strength. Finally, it would also be possible simply to apply less adhesive (i.e. of a reduced surface area) in the terminal zone.

Most preferably, the sanitary absorbent article is a feminine sanitary napkin, i.e. it is placed in the pudendal region of a female and is used to absorb menses and other discharged fluids.

Other objects and features of the invention will become apparent by reference to the following description and the drawings.

BRIEF DESCRIPTION OF THE DRAWINGS

A detailed description of preferred embodiments of the present invention is provided hereinbelow with reference to the following drawings, in which:

FIG. 1a is a cross-sectional view of the napkin of FIG. 1 taken along the line 1a—1a;

In the drawings, preferred embodiments of the invention are illustrated by way of example. It is to be expressly understood that the description and drawings are only for purposes of illustration and as aids to understanding, and are not intended to be a definition of the limits of the invention.

DETAILED DESCRIPTION OF PREFERRED EMBODIMENTS

Figure 1:
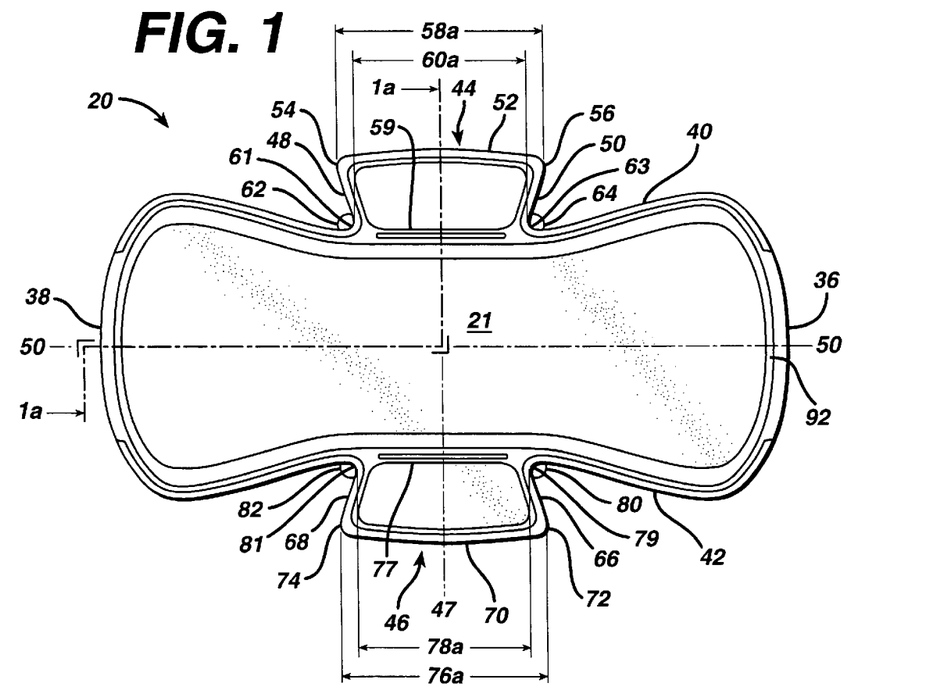
FIG. 1 is a top plan view of a preferred embodiment of the present invention, a feminine sanitary napkin.
Figure 1A:
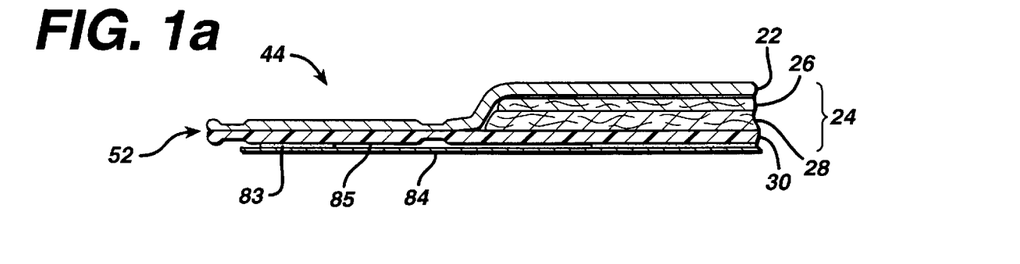

As shown in FIG. 1, the preferred embodiment of the present invention is a feminine sanitary napkin 20. Referring to FIG. 1a, the napkin is of a laminate construction and preferably comprises a fluid-permeable cover layer 22, an absorbent system 24, and a fluid-impervious barrier layer 30.

Cover Layer

The cover layer 22 may be a relatively low density, bulky, high-loft non-woven web material. The cover layer 22 may be composed of only one type of fibre, such as polyester or polypropylene or it may be composed of bi-component or conjugate fibres having a low melting point component and a high melting point component. The fibres may be selected from a variety of natural and synthetic materials such as nylon, polyester, rayon (in combination with other fibres), cotton acrylic fibre and the like and combinations thereof.

Bi-component fibres may be made up of a polyester core and a polyethylene sheath. The use of appropriate bi-component materials results in a fusible non-woven fabric. Examples of such fusible fabrics are described in U.S. Pat. No. 4,555,430 issued Nov. 26, 1985 to Mays. Using a fusible fabric increases the ease with which the cover layer may be mounted to the adjacent transfer layer and/or to the barrier layer.

The cover layer 22 preferably has a relatively high degree of wettability, although the individual fibres comprising the cover may not be particularly hydrophilic. The cover material should also contain a great number of relatively large pores. This is because the cover layer 22 is intended to absorb body fluid rapidly and transport it away from the body and the point of deposition. Preferably, the fibres which make up the cover layer 22 should not lose their physical properties when they are wetted, in other words, they should not collapse or lose their resiliency when subjected to water or body fluid. The cover layer 22 may be treated to allow fluid to pass through it readily. The cover layer 22 also functions to transfer the fluid quickly to the other layers of the absorbent structure 24. Thus, the cover layer 22 is preferably wettable, hydrophilic and porous. When composed of synthetic hydrophobic fibres such as polyester or bi-component fibres, the cover layer 22 may be treated with a surfactant to impart the desired degree of wettability.

Most preferably, the cover layer 22 is made of polymer film having large pores. Because of such high porosity, the film accomplishes the function of quickly transferring body fluid to the inner layers of the absorbent system. Apertured co-extruded films such as RETICULON™ brand, for example, described in U.S. Pat. No. 4,690,679 are useful as cover layers in the absorbent structures of this invention.

The cover layer 22 may be embossed to the remainder of the absorbent system 24 in order to aid in promoting hydrophilicity by fusing the cover to the next layer.

Absorbent System—Transfer Layer

Adjacent to the cover layer 22 on its inner side and bonded to the cover layer 22 is a fluid transfer layer 26 that forms part of the absorbent system 24. The transfer layer 26 provides the means of receiving body fluid from the cover layer 22 and holding it until the highly-dense absorbent core 28 has an opportunity to absorb the fluid.

The transfer layer 26 is, preferably, more dense than and has a larger proportion of smaller pores than the cover layer 22. These attributes allow the transfer layer 26 to contain body fluid and hold it away from the outer side of the cover layer 22, thereby preventing the fluid from re-wetting the cover layer 22 and its surface. However, the transfer layer 26 is, preferably, not so dense as to prevent the passage of the fluid through the layer 26 into the absorbent core 28.

The transfer layer 26 may be composed of fibrous materials, such as wood pulp, polyester, rayon, flexible foam, or the like, or combinations thereof. The transfer layer 26 may also comprise thermoplastic fibers for the purpose of stabilizing the layer and maintaining its structural integrity. The transfer layer 26 may be treated with surfactant on one or both sides in order to increase its wettability, although generally the transfer layer 26 is relatively hydrophillic and may not require treatment. The transfer layer 26 is preferably bonded on both sides to the adjacent layers, i.e. the cover layer 22 and the absorbent core 28.

Absorbent System—Absorbent Core

Immediately adjacent to and bonded to the transfer layer 26 is the absorbent core 28. The absorbent core 28 is preferably a highly dense layer having a fine porosity. It has a large liquid holding capacity and it is extremely retentive. Most preferably, the absorbent core 28 is composed of compressed sphagnum moss material. More specifically, the sphagnum moss is formed as a board by air or wet laying and calendering to obtain a relatively thin, i.e. from about 0.025 cm to 0.25 cm thick, relatively dense, i.e. from about 0.2 to 1.0 g/cm$^3$ sheet-like structure. The structure may include a layer of Kraft tissue laminated on one or both surfaces of the sphagnum moss layer. Preferably, a fibrous component is admixed with the sphagnum moss material. The fibrous component is suitably a natural or synthetic textile fiber such as rayon, polyester, nylon, acrylic or the like, having a length of from about 0.62 to 3.75 cm and a denier of from about 1.0 to 5. The fibrous component may be present in an amount from about 2 to 20% by weight, most preferably from 4 to 8%. The absorbent core 28 may also comprise other components such as wood pulp, synthetic wood pulp, thermo-mechanical pulp, mechanically ground pulp, polymers, surfactants, superabsorbents and the like.

In an alternative embodiment, the absorbent system 24 includes a single layer of pulp fluff material (the transfer layer is omitted). The absorbent core 28 preferably comprises a pulp fluff material and may optionally include other absorbent materials or non-absorbent materials which aid in stabilizing the absorbent structure such as conjugate fibers, fusible fibers, binders, sphagnum peat moss particles, superabsorbents, and the like and combinations thereof, and may optionally include other absorbent materials or non-absorbent materials which aid in stabilizing the absorbent structure such as conjugate fibers, fusible fibers, binders, sphagnum peat moss particles, superabsorbents, and the like and combinations thereof

Barrier Layer

Underlying the absorbent system 24 is a barrier layer 30 comprising fluid-impervious film material so as to prevent liquid that is entrapped in the absorbent core from egressing the sanitary napkin and staining the wearer's undergarment. Most preferably, the barrier layer 30 is made of polymeric film, such as polyethylene which is both inexpensive and readily available. The polyethylene is capable of fully blocking the passage of liquid or gas that may emanate from the absorbent system 24. In a variant, breathable films may be used that allow passage of gases while blocking liquid.

The cover layer 22 and the barrier layer 30 are joined along their marginal portions so as to form an enclosure that maintains the absorbent system 24 captive. The joint may be made by means of adhesives, heat-bonding, ultrasonic bonding, radio frequency sealing, mechanical crimping, and the like and combinations thereof The peripheral seal line is shown in FIG. 1 by the reference numeral 92.

Flap Configuration

Referring again to FIG. 1 and FIG. 1b, the sanitary napkin 20 is comprised of a main body 21 having a first transverse side 36 and an opposing second transverse side 38. Each transverse side 36, 38 is arcuate in shape (curved outward such that the two transverse sides 36, 38 are biconvex), with no particular curvature being essential to the present invention. The sanitary napkin 20 further has an arcuate first longitudinal side 40 and an opposing arcuate second longitudinal side 42, each being curved inward (i.e. the longitudinal sides 40, 42 are biconcave), with no particular curvature being essential to the present invention. The shape of the main body 21 of the napkin 20 when viewed from above, as shown in FIG. 1, is thus somewhat hourglass-like. The contour of the sanitary napkin 20 is symmetric about an imaginary longitudinal centerline 50 extending longitudinally down the sanitary napkin 20, and a transverse centerline 47 extending transversely across the napkin 20.

Figure 1B:
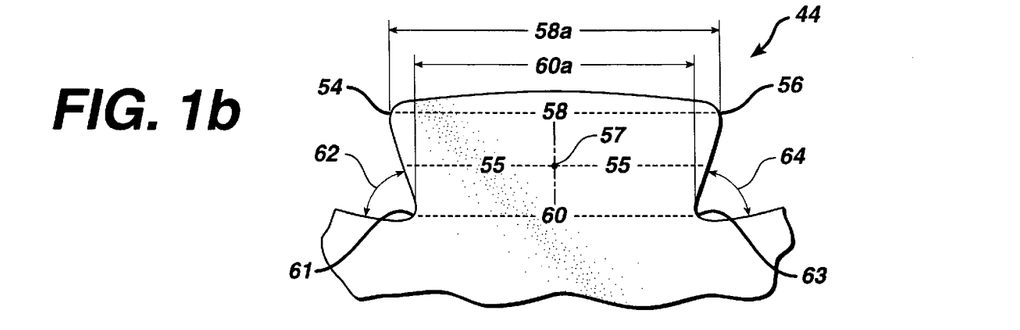
FIG. 1b is an enlarged top plan view of the first flap of the napkin of FIG. 1 (the peripheral seal line having been removed for clarity)

A first flap 44 projects laterally from the central region of first longitudinal side 40 of the main body 21. The first flap 44 is generally of the shape of an isosceles (i.e. bilaterally symmetrical) trapezoid. The first flap 44 thus has a distal end 52 formed of the base of the trapezoid. The distal end 52 is preferably slightly convexo-arcuate. The sides of the trapezoid are substantially straight and form the first transverse side 48 and second transverse side 50 of the first flap 44. The top of the trapezoid forms the proximate side 59 of the first flap 44. As the first flap 44 is formed from an integral extension of the cover layer 22 and the barrier layer 30 of the main body 21, the proximate side 59 of the first flap 44 adjoins the first longitudinal side 40 of the main body 21 of the napkin 20.

The first transverse side 48 of the first flap 44 intersects the distal side 52 of the first flap 44 at a (first) point of intersection 54. Similarly, the second transverse side 50 of the first flap 44 intersects the distal side 52 of the first flap 44 at a (second) point of intersection 56. A first (imaginary) line 58 may be drawn between these points of intersection 54, 56. (The length of this line being illustrated by reference number 58a, and is approximately 7.0 cm) The first transverse side 48 of the first flap 44 intersects the first longitudinal side 40 of the main body 21 at (third) point of intersection 61. Similarly, the second transverse side 50 of the first flap 44 intersects the first longitudinal side 40 of the main body 21 at a (fourth) point of intersection 63. A second (imaginary) line 60 (representing the proximal side 59) may be drawn between these points of intersection 61, 63. (The length of this line being illustrated by reference number 60a, and is approximately 6.2 cm.) The length 58a of the first line 58 is greater than the length 60a of the second line 60.

The first flap 44 has a midpoint 57 which is equidistant from the first imaginary line 58 and the second imaginary line 60 while at the same time being equidistant from the first transverse side 48 and the second transverse side 50 of the first flap 44. An imaginary line 55 parallel to the longitudinal centreline 50 may be drawn through the midpoint 57.

The angle 62 formed by the intersection of the first transverse side 48 of the first flap 44 and the first longitudinal side 40 of the main body 21 and the angle 64 formed by the intersection of the second transverse side 50 of the first flap 44 and the first longitudinal side 40 of the main body 21 are each approximately 75°.

A second flap 46 projects laterally form the central region of the second longitudinal side 42 of the main body 21. The second flap 46 is generally of the shape of an isosceles trapezoid. The second flap 46 thus has a distal end 70 formed of the base of the trapezoid. The distal end 70 is preferably slightly convex-arcuate. The sides of the trapezoid are substantially straight and form the first transverse side 66 and the second transverse side 68 of the second flap 46. The top of the trapezoid forms the proximate side 77 of the second flap 46. As the second flap 46 is formed from an integral extension of the cover layer 22 and the barrier layer 30 of the main body 21, the proximate side 77 of the second flap 46 adjoins the second longitudinal side 42 of the main body 21 of the napkin 20.

The first transverse side 66 of the second flap 46 intersects the distal side 77 of the second flap 46 at a (first) point of intersection 72. Similarly, the second transverse side 68 of the second flap 46 intersects the distal side 70 of the second flap 46 at a (second) point of intersection 74. A first (imaginary) line (not shown) may be drawn between these points of intersection 72, 74. (The length of this line is illustrated by reference number 76a, and is approximately 7.0 cm) The first transverse side 66 of the second flap 46 intersects the second longitudinal side 42 of the main body 21 at a (third) point of intersection 79. Similarly, the second transverse side 68 of the second flap 46 intersects the second longitudinal side 42 of the main body 21 at a (fourth) point of intersection 81. A second (imaginary) line (not shown) may be drawn between these points of intersection 79, 81. (The length of this line is illustrated by reference number 78a and is approximately 6.2 cm.) The length 76a of the first line is greater than the length 78a of the second line.

The second flap 46 has a midpoint (not shown) which is equidistant from the first imaginary line and the second imaginary line while at the same time being equidistant from the first transverse side 66 and the second transverse side 68 of the second flap 46.

The angle 80 formed by the intersection of the first transverse side 66 of the second flap 46 and the second longitudinal side 42 of the main body 21 and the angle 82 formed by the intersection of the second transverse side 42 of the second flap 46 and the second longitudinal side 42 of the main body 21 are each approximately 75°.

Adhesive Fasteners

Figure 2:
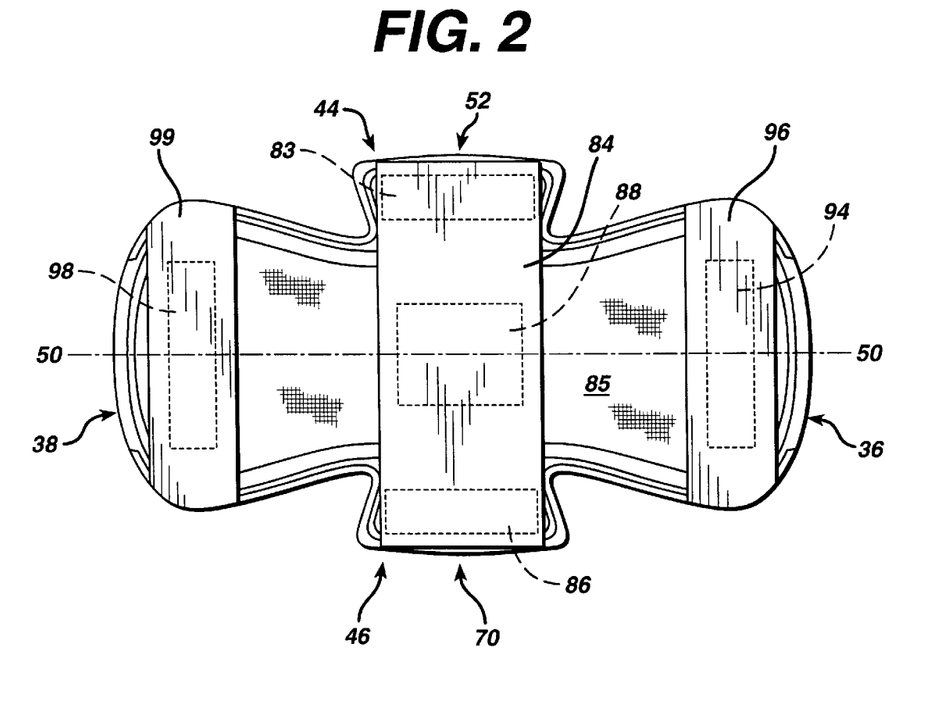
FIG. 2 is a bottom plan view of the napkin of FIG. 1.

Referring to FIG. 2, in order to enhance the stability of the sanitary napkin 20, on the garment-facing side 85 of the barrier layer 30 of the main body 21, there are provided five fasteners 83, 86, 88, 94, 98 for fastening the napkin 20 to the undergarment 18 of a wearer when the napkin 20 is in use. Each of these fasteners 83, 86, 88, 94, 98 are of a conventional design e.g. they comprise adhesive material, such as hot-melt adhesives capable of establishing a temporary bond with the undergarment 18 material. One 88 of these fasteners is located in the central region of the main body 21 of the napkin 20, a second 94 and third 98 in the area of the transverse sides 38, 38 of the main body 21 of the napkin 20, and a fourth 83 and a fifth 86 in the area of the distal edge 52, 70 of the first flap 44 and second flap 46, respectively. Separate release papers 96, 99 cover the second 94 and the third 98 fasteners, while a single release paper 84 covers the first 88, fourth 83, and fifth 86.

Figure 2A:
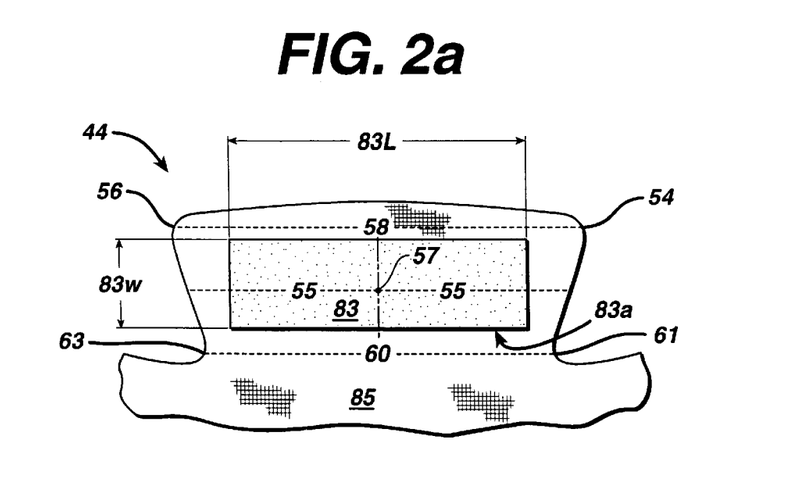
FIG. 2a is an enlarged bottom plan view of the first flap of the napkin of FIG. 1b (the peripheral seal line having been removed for clarity)

Referring to FIG. 2a, there is shown the garment-facing surface 85 of the first flap 44 shown in FIG. 1b, including the fourth adhesive 83. (The release paper 84 having been removed.) The adhesive has been applied in a generally rectangular shape, the longer side 83a of which is parallel to the longitudinal centreline of the article 20. The fourth adhesive 83 has a width 83w (i.e. measurement taken in a direction parallel to the transverse centreline of the article) of 1.5 cm and a length 83l (i.e. measurement taken in a direction parallel to the longitudinal centreline of the article) of 4.8 cm. Although not shown, the fifth adhesive 86 would be of similar construction.

Alternate Embodiments

Figure 2B:
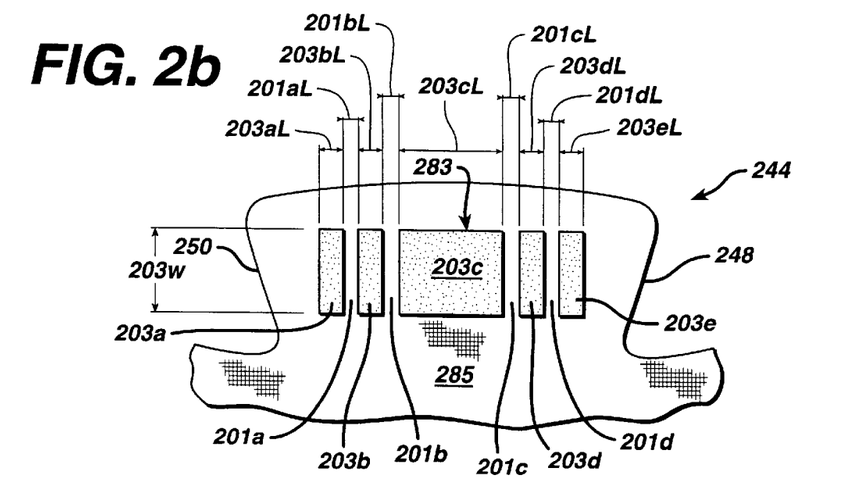
FIG. 2b is an enlarged bottom plan view of the first flap of an alternative embodiment of the present invention, similar to FIG. 2a (the peripheral seal line having been removed for clarity)

Referring to FIG. 2b, there is shown a garment-facing surface 285 of a flap 244 (similar to that shown in FIG. 2a) having an alternate embodiment of the present invention. Specifically the "fourth" adhesive 283 has been applied in a discontinuous fashion, i.e. there are gaps 201a, 201b, 201c, 201d, in the continuity of the adhesive 283. The adhesive 283 now takes the appearance of a plurality of rectangles 203a, 203b, 203c, 203d, 203e. The centre rectangle 203c having a width 203w of 1.5 cm and a 203cl length of 1.6 cm. Each of the other rectangles 203a, 203b, 203d, 203e (there are two are on either side of the central one) having a width 203w of 1.5 cm and a length 203al, 203bl, 203dl, 203el respectively, of 0.5 cm. The rectangles 203a, 203b, 203c, 203d, 203e each being separated by a distance of 0.3 cm. The purpose of these gaps 201a, 201b, 201c, 201d is to reduce the adhesive strength of the adhesive 283 in the areas closer to the transverse sides 248, 250 of the flap 244. The adhesive 283 itself is otherwise the same as described hereinabove in reference to FIG. 2a. Similarly, although not shown, a "fifth" adhesive would be of similar construction.

Figure 3:
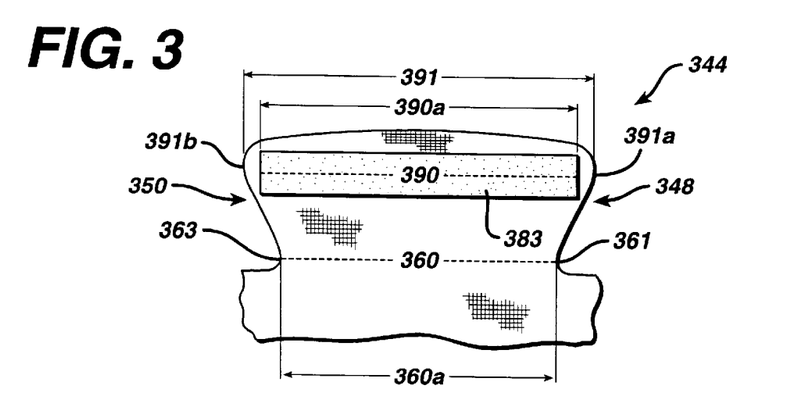
FIG. 3 is an enlarged bottom plan view, similar to that of FIG. 2a, of a first flap of a third embodiment of the present invention (the peripheral seal line having been removed for clarity)

Referring to FIG. 3, there is shown another embodiment of the present invention. In this embodiment the "fourth" fastener 383, i.e. that on the first flap 344, has a longitudinal length 390a which exceeds the length 360a of the second line 360 (representing the proximal side) on the first flap 344. Moreover, the transverse sides 348 and 350 are only substantially straight between their respective points of intersection 361, 363 with the proximal side 359 and their respective points of intersection 391a, 391b with the line 391 along which the longitudinal length 390 of the adhesive 383 is measured. Similarly, although not shown, a "fifth" adhesive would be of similar construction.

Figure 4:
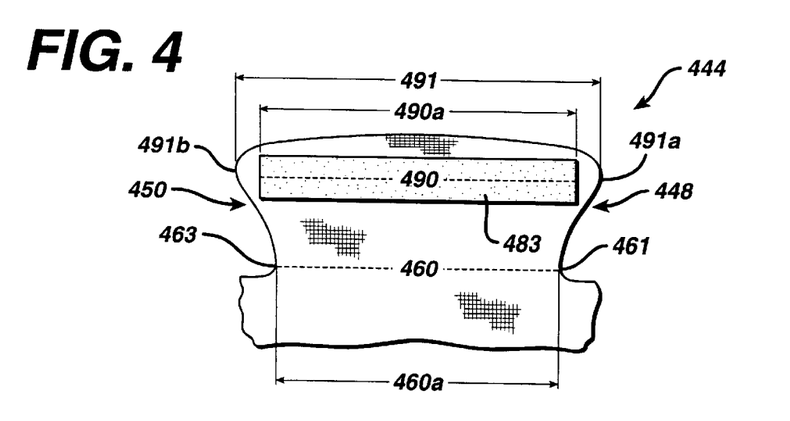
FIG. 4 is an enlarged bottom plan view, similar to that of FIG. 2a, of a first flap of a fourth embodiment of the present invention (the peripheral seal line having been removed for clarity)
Figure 5:
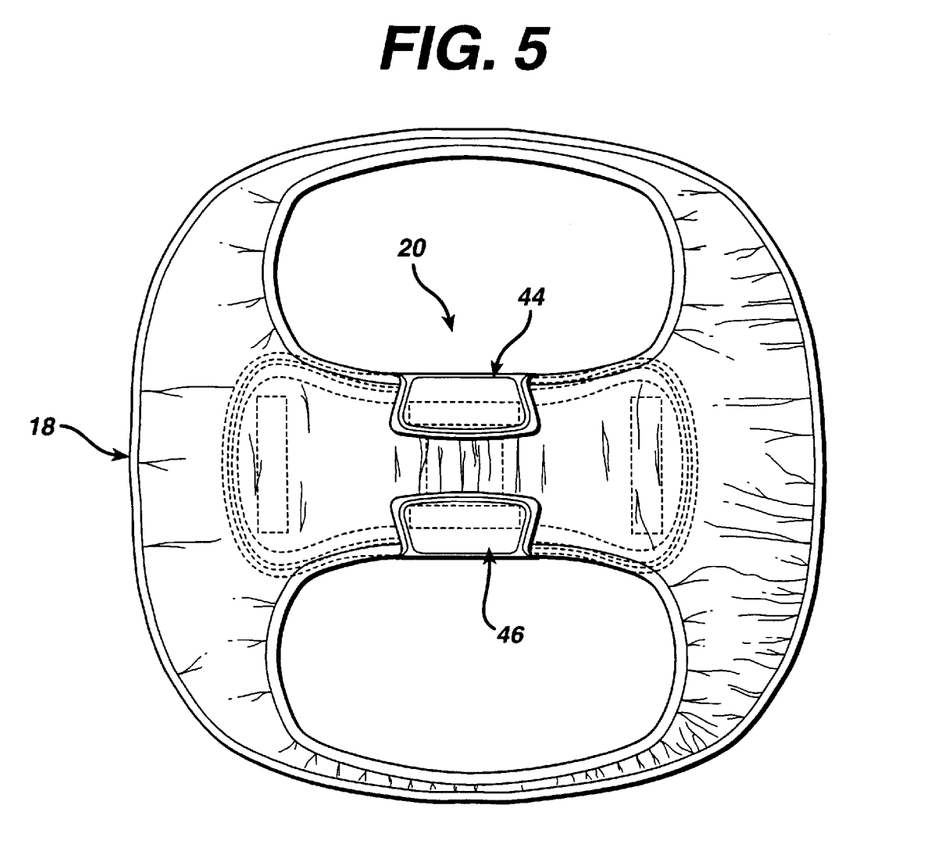
FIG. 5 is a bottom plan view of the napkin of FIG. 1 when placed within a typical undergarment.

FIG. 4 illustrates another alternate embodiment of the invention in which the first transverse side 448 of the flap 444 and the second transverse side 450 of the flap 444 are arcuate (as opposed to substantially straight.) These transverse sides 448, 450 are substantially continually divergent in accordance with the teachings of the present invention. (i.e. between their respective points of intersection 461, 463 with the proximal side 459 and their respective points of intersection 491a, 491b with the line 491 along which the longitudinal length 490 of the adhesive 483 is measured.) Moreover, the maximum longitudinal length 490a of the fastener 483 exceeds the length 460a of the line 460 connecting the points of intersection 461, 463 (respectively) of the first transverse side 448 and the second transverse side 450 with the first longitudinal side 440 of the main body of the article (i.e. the proximal side of the flap 444). Similarly, although not shown, a "fifth" adhesive would be of similar construction.

To use the sanitary napkin 20, the release papers 84, 96, 99 are removed exposing the fasteners 83, 86, 88, 94, 98. As shown in FIG. 6, the napkin 20 is then positioned in the pudendal region of the undergarment 18, and the first flap 44 and the second flap 46 are folded about the sides thereof. The fasteners 83, 86, 88, 94, 98 adhere to the undergarment 18, securing the napkin 20 in place.

The above description of preferred embodiments should not be interpreted in a limiting manner since other variations, modifications and refinements are possible within the spirit and scope of the present invention. The scope of the invention is defined in the appended claims and their equivalents.

What is claimed is:

1. A sanitary absorbent article comprising:
   (A) a main body, said main body having a first longitudinal side, a second longitudinal side generally opposing the first longitudinal side, two generally-opposing transverse sides, and a longitudinal centerline; and
   (B) a first flap united with said main body, said first flap affixed to and projecting laterally from the first longitudinal side of said main body when the article is in a flattened state and being capable of being folded over a crotch portion of a wearer's undergarment,
   (C) a second flap united with said main body, said second flap affixed to and projecting laterally from the second longitudinal side of said main body when the article is in a flattened state and being capable of being folded over the crotch portion of the undergarment, each flap having:
   (i) a distal side;
   (ii) a proximal side generally opposing the distal side, the proximal side being affixed to the respective longitudinal side of said main body;
   (iii) a first transverse side;
   (iv) a second transverse side generally opposing the first transverse side; and
   (v) a garment-facing surface including a fastener for securing said each flap to the undergarment, said fastener having a longitudinal length that is at least 85% of the length of the proximal side;
   the main body and each proximal side having a respective length wherein the length of each proximal side is less than one half the length of the main body;
   the first transverse side and the second transverse side being substantially continually divergent from the proximal side until at least an imaginary line parallel to the longitudinal centerline of said main body at approximately a midpoint of said each flap; wherein
   (A) the fastener of said first flap further comprises:
      (1) a central zone having an adhesive strength; and
      (2) a terminal zone having an adhesive strength, the adhesive strength of the terminal zone being less than the adhesive strength of the central zone;
   (B) the fastener of said second flap further comprises:
      (1) a central zone having an adhesive strength; and
      (2) a terminal zone having an adhesive strength, the adhesive strength of the terminal zone being less than the adhesive strength of the central zone, and
   wherein the terminal zone of each of the fasteners includes a plurality of discontinuities for reducing the adhesive strength of the terminal zone relative to the central zone.

2. A sanitary absorbent article as recited in claim 1, wherein, when the article is in a flattened state:
   (a) the transverse sides of said first flap each intersect with the first longitudinal side of said main body to form an angle of not less than about 60°; and
   (b) the transverse sides of said second flap each intersect with the second longitudinal side of said main body to form an angle of not less than about 60°.

3. A sanitary absorbent article as recited in claim 2, wherein, when the article is in a flattened state,
   (a) the transverse sides of said first flap each intersect with the first longitudinal side of said main body to form an angle of about 75°; and
   (b) the transverse sides of said second flap each intersect with the second longitudinal side of said main body to form an angle about 75°.

4. A sanitary absorbent article as recited in claim 1, wherein:
   (a) the fastener of said first flap has a longitudinal length not less than the length of the proximal side of said first flap; and
   (b) the fastener of said second flap has a longitudinal length not less than the length of the proximal side of said second flap.

5. A sanitary absorbent article comprising:
   (A) a main body, said main body having a first longitudinal side, a second longitudinal side generally opposing the first longitudinal side, two generally-opposing transverse sides, and a longitudinal centerline; and
   (B) a first flap united with said main body, said first flap affixed to and projecting laterally from the first longitudinal side of said main body when the article is in a flattened state and being capable of being folded over a crotch portion of a wearer's undergarment, (C) a second flap united with said main body, said second flap affixed to and projecting laterally from the second longitudinal side of said main body when the article is in a flattened state and being capable of being folded over the crotch portion of the undergarment, each flap having:
  (i) a distal side;
  (ii) a proximal side generally opposing the distal side, the proximal side being affixed to the respective longitudinal side of said main body;
  (iii) a first transverse side;
  (iv) a second transverse side generally opposing the first transverse side; and
  (v) a garment-facing surface including a fastener for securing said each flap to the undergarment, said fastener having a longitudinal length that is at least 85% of the length of the proximal side;

the first transverse side and the second transverse side being substantially continually divergent from the proximal side until at least an imaginary line parallel to the longitudinal centerline of said main body at approximately a midpoint of said each flap;

(D) the first transverse side of said first flap and the second transverse side of said first flap are substantially straight from the proximal side of said first flap until the imaginary line; and (E) the first transverse side of said second flap and the second transverse side of said second flap are substantially straight from the proximal side of said second flap until the imaginary line.

6. A sanitary absorbent article comprising:

(A) a main body, said main body having a first longitudinal side, a second longitudinal side generally opposing the first longitudinal side, two generally-opposing transverse sides, and a longitudinal centerline; and (B) a first flap united with said main body, said first flap affixed to and projecting laterally from the first longitudinal side of said main body when the article is in a flattened state and being capable of being folded over a crotch portion of a wearer's undergarment, (C) a second flap united with said main body, said second flap affixed to and projecting laterally from the second longitudinal side of said main body when the article is in a flattened state and being capable of being folded over the crotch portion of the undergarment, each flap having:
  (i) a distal side;
  (ii) a proximal side generally opposing the distal side, the proximal side being affixed to the respective longitudinal side of said main body;
  (iii) a first transverse side;
  (iv) a second transverse side generally opposing the first transverse side; and
  (v) a garment-facing surface including a fastener for securing said each flap to the undergarment, said fastener having a longitudinal length that is at least 85% of the length of the proximal side;

(D) the first transverse side of said first flap and the second transverse side of said first flap are substantially continually divergent from the proximal side of said first flap until the distal side of said first flap; and (E) the first transverse side of said second flap and the second transverse side of said second flap are substantially continually divergent from the proximal side of said second flap until the distal side of said second flap.

7. A sanitary absorbent article as recited in claim 6, wherein:

(A) the first transverse side of said first flap and the second transverse side of said first flap are substantially straight from the proximal side of said first flap until the distal side of the first flap; and (B) the first transverse side of said second flap and the second transverse side of said second flap are substantially straight from the proximal side of said second flap until the distal side of said second flap.

8. A sanitary absorbent article as recited in claims 7, wherein the distal side of each of said flaps is each substantially straight.

* * * * *